United States Patent
Welch et al.

(10) Patent No.: US 9,714,203 B2
(45) Date of Patent: Jul. 25, 2017

(54) METHOD FOR REDUCING ENERGY CONSUMPTION IN THE PRODUCTION OF STYRENE MONOMER UTILIZING AZEOTROPIC WATER/ETHYLBENZENE FEED VAPORIZATION

(71) Applicant: Technip Process Technology, Inc., Houston, TX (US)

(72) Inventors: Vincent Welch, Medway, MA (US); Slawomir A. Oleksy, Billerica, MA (US)

(73) Assignee: Technip Process Technology, Inc., Houston, TX (US)

( * ) Notice: Subject to any disclaimer, the term of this patent is extended or adjusted under 35 U.S.C. 154(b) by 0 days.

(21) Appl. No.: 14/772,835

(22) PCT Filed: Mar. 15, 2013

(86) PCT No.: PCT/US2013/032244
§ 371 (c)(1),
(2) Date: Sep. 4, 2015

(87) PCT Pub. No.: WO2014/142994
PCT Pub. Date: Sep. 18, 2014

(65) Prior Publication Data
US 2016/0016863 A1 Jan. 21, 2016

(51) Int. Cl.
*C07C 5/367* (2006.01)
*C07C 5/327* (2006.01)
*C07C 5/333* (2006.01)

(52) U.S. Cl.
CPC .............. *C07C 5/333* (2013.01); *C07C 5/327* (2013.01)

(58) Field of Classification Search
CPC ................................ C07C 5/367; C07C 5/327
USPC .................................................. 585/441, 440
See application file for complete search history.

(56) References Cited

U.S. PATENT DOCUMENTS

| | | |
|---|---|---|
| 4,628,136 A | 12/1986 | Sardina |
| 4,695,664 A | 9/1987 | Whittle |
| 8,084,660 B2 | 12/2011 | Welch et al. |
| 8,163,971 B2 | 4/2012 | Wilcox et al. |
| 2011/0245561 A1 | 10/2011 | Merrill et al. |
| 2012/0149960 A1 | 6/2012 | Gami et al. |

FOREIGN PATENT DOCUMENTS

| | | |
|---|---|---|
| CN | 102333746 A | 1/2012 |
| WO | WO 2010/107651 A2 | 9/2010 |

OTHER PUBLICATIONS

Notification of First Office Action issued from the State Intellectual Property Office of P.R. China dated Jun. 29, 2016 for Chinese Application No. 201380074335.1 filed Jan. 14, 2016 for applicant, Technip Process Technology, Inc. (in Chinese and its English language translation).
PCT Notification Concerning Transmittal of the International Search Report and the Written Opinion of the International Searching Authority, or the Declaration; PCT International Search Report; PCT Written Opinion of the International Searching Authority.

*Primary Examiner* — Thuan D Dang
(74) *Attorney, Agent, or Firm* — Locke Lord LLP; Alan B. Clement; Peter J. Fallon

(57) ABSTRACT

The present invention is directed to reduced-energy improvements in methods and systems to produce styrene monomer via ethylbenzene dehydrogenation. The methods and systems reduce utility cost and provide savings in comparison with the current technology practiced in the industry.

20 Claims, 3 Drawing Sheets

US 9,714,203 B2

METHOD FOR REDUCING ENERGY CONSUMPTION IN THE PRODUCTION OF STYRENE MONOMER UTILIZING AZEOTROPIC WATER/ETHYLBENZENE FEED VAPORIZATION

TECHNICAL FIELD

The present invention relates to reduced-energy improvements in methods and systems to produce styrene monomer via ethylbenzene dehydrogenation. The methods and systems reduce utility cost and provide savings in comparison with the current technology practiced in the industry.

BACKGROUND

It is well known in the art of styrene manufacture to react ethylbenzene (EB) in the presence of steam over a dehydrogenation catalyst, such as iron oxide under dehydrogenation reaction conditions, in order to strip hydrogen from the ethyl group on the benzene ring to form styrene. It is also well known that the dehydrogenation of ethylbenzene requires large amounts of energy, for example, in the form of steam.

Alternate methods for reducing energy consumption (i.e., steam) in processes for producing styrene via dehydrogenation of ethylbenzene have been previously described.

U.S. Pat. No. 4,628,136 to Sardina discloses a dehydrogenation process for producing styrene from ethylbenzene in the presence of steam by recovering heat of condensation normally lost during separation of the various components and using the heat to vaporize an aqueous feed mixture of ethylbenzene and dilution water. Sardina teaches that this obviates the need to use steam to vaporize the liquid ethylbenzene feed.

U.S. Pat. No. 8,163,971 to Wilcox et al. addresses the problem of supplying heat to the system at an overall steam/oil weight ratio of 1.0 or lower. Generally, these ratios would require steam temperature at the outlet of the steam superheater to be increased to 950° C., or even higher. However, superheater temperatures above 927° C. require the use of special and costly metallurgy.

U.S. Pat. No. 8,084,660 to Welch et al. discloses methods for increasing the efficiency and/or expanding the capacity of a dehydrogenation unit by use of at least one direct heating unit. The disclosed methods lower the steam to hydrocarbon ratio of the process to reduce the costs incurred in generating and superheating steam.

U.S. Pat. No. 7,922,980 to Oleksy et al. discloses methods for recovering the heat of condensation from overhead vapor produced during ethylbenzene-to-styrene operations. In this regard, the '980 patent uses the overhead of an EB/SM splitter column to vaporize an azeotropic mixture of ethylbenzene and water.

For economic reasons, however, it is still desirable to lower the steam to hydrocarbon ratio of the process due to the costs incurred in generating and superheating steam. Thus, the inventive methods disclosed herein provide for a reduction of reaction steam/EB ratio while practicing azeotrope heat recovery without resorting to the use of tremendously expensive alloys.

SUMMARY OF THE INVENTION

The present invention is directed to reduced-energy improvements in processes to produce styrene monomer via ethylbenzene dehydrogenation utilizing azeotrope heat recovery.

The present invention is directed to a method for reducing the amount of steam used in a dehydrogenation section of an alkenyl aromatic hydrocarbon production facility. The dehydrogenation section is used for dehydrogenating ethylbenzene to styrene monomer, and the method comprises: i) heating a feed stream comprising ethylbenzene and water as an azeotrope to provide an ethylbenzene/feed steam stream containing vaporized ethylbenzene and feed steam having a feed steam to ethylbenzene ratio of about 0.4 to about 0.6; and ii) dehydrogenating the ethylbenzene in the dehydrogenation section comprising at least a first, second, and a third reactor, at least two reheat exchangers, and a mixing apparatus upstream of the first reactor, said reheat exchangers utilizing superheated heating steam as a heating medium, and said mixing apparatus is used for mixing heating steam with the ethylbenzene/feed steam stream; wherein the temperature of the heating steam in the dehydrogenation section is less than about 899° C. and said method utilizes a total heating steam to ethylbenzene ratio of less than about 0.65.

According to another embodiment, the present invention is directed to a method for reducing the amount of steam used in a dehydrogenation section of an alkenyl aromatic hydrocarbon production facility. The dehydrogenation section for dehydrogenating ethylbenzene to styrene monomer and the method comprises: i) heating a feed stream comprising ethylbenzene and water as an azeotrope to provide an ethylbenzene/feed steam stream containing vaporized ethylbenzene and feed steam having a feed steam to ethylbenzene ratio of about 0.4 to about 0.6; mixing the ethylbenzene/feed steam stream with heating steam from a steam superheater; supplying the ethylbenzene/feed steam stream and heating steam to a first reactor in the dehydrogenation section; iv) dehydrogenating the ethylbenzene in the first reactor, a second reactor, and at least a third reactor of the dehydrogenation section to produce styrene monomer; and, v) reheating an effluent from the first reactor in at least a first reheat exchanger and an effluent from the second reactor in at least a second reheat exchanger, wherein each reheat exchanger is provided with heating steam from at least one steam superheater, said heating steam having a temperature of less than about 899° C. and said method utilizing a total heating steam to ethylbenzene ratio of less than about 0.65.

Further, the present invention is directed to a system for reducing the amount of steam used in a dehydrogenation section of an alkenyl aromatic hydrocarbon production facility. The dehydrogenation section for dehydrogenating ethylbenzene to styrene monomer and the system sequentially comprises: a means for heating a feed stream comprising ethylbenzene and water as an azeotrope to provide an ethylbenzene/feed steam stream containing vaporized ethylbenzene and feed steam having a feed steam to ethylbenzene ratio of about 0.4 to about 0.6; a mixing apparatus for mixing the ethylbenzene/feed steam stream with superheated heating steam, the heating steam is utilized as a heating medium; a means for supplying the ethylbenzene/feed steam stream and heating steam to a first dehydrogenation reactor to provide effluent to a first reheat exchanger for reheating said effluent prior to entering a second dehydrogenation reactor and providing a second reactor effluent that is reheated in a second reheat exchanger prior to entering a third dehydrogenation reactor to provide styrene monomer, said first and second reheat exchangers utilizing superheated heating steam as a heating medium, and wherein the heating steam has a temperature of less than about 899° C. and said system utilizes a total heating steam to ethylbenzene ratio of less than about 0.65.

The improvements disclosed herein are substantial in terms of their economic impact, i.e., up to 25% reduction in the amount of fuel (see, for example, Net Heat Input (as Fuel) (kcal/kg EB) Table 1) used in the reactor section, compared to the industry standard. Just as importantly, these improvements do not require fundamental changes to the process, for example, increased temperatures or pressures. Therefore, it is anticipated that there will be little resistance to adopting them.

DETAILED DESCRIPTION

Figure 1:
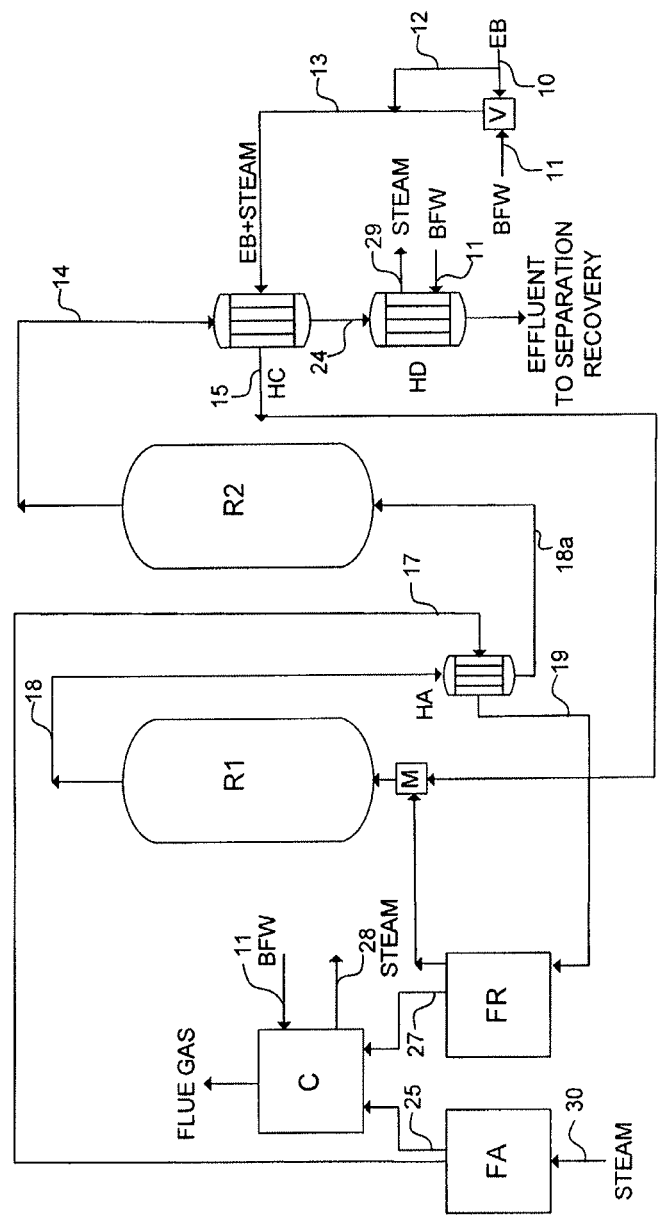
FIG. 1 is a schematic flowsheet illustrating the reaction section of a prior art two-reactor system for the production of styrene via dehydrogenation of ethylbenzene.

Ethylbenzene dehydrogenation requires large amounts of energy in the form of steam. In particular, the dehydrogenation process requires large amounts of excess "reaction steam," which is the total amount of steam needed to drive the endothermic reaction (i.e., the heat required to moderate the temperature drop as the reaction proceeds), reduce the partial pressure of the reactants, and prevent catalyst coking. Reaction steam is supplied to the dehydrogenation process in two forms: "heating steam," which is used as a heat transfer media to heat the reactor feeds in either heat exchangers and/or fired heaters, and "feed steam," which accompanies the ethylbenzene (EB) feed to prevent coking in high temperature heat transfer equipment.

Due to the temperature limitations of the metallurgies used in the styrene process heat exchange equipment and piping, which are set by ASME codes, there is a minimum amount of heating steam that must be supplied to accomplish the required heat transfer while simultaneously remaining below the threshold ASME code metal temperatures. In a two stage dehydrogenation reactor flow scheme, i.e., a primary reactor followed by a secondary reactor, the minimum ratio of heating steam to ethylbenzene feed for a plant using Incoloy 800H/800 HT metallurgy, which has a ASME code limit of 899° C., is approximately 0.65 to 0.70 on a weight basis.

One particularly valuable way to recover low temperature energy from a styrene plant is to vaporize the ethylbenzene feed as an azeotrope with water. The advantage of boiling the water/EB azeotrope is that the mixture boils at a temperature significantly lower than either of the two pure components, thus making recovery of low temperature heat more economic. While slightly dependent on pressure, the composition of the water (i.e., feed steam)/EB azeotrope is about 0.50 on a weight basis.

When azeotropic EB feed vaporization is practiced in a two stage reactor system, where 100% of the EB feed is vaporized as an azeotrope, the minimum total Reaction Steam/EB ratio, also known as Steam-to-Oil ratio, is the sum of the minimum "heating steam" and "feed steam," which is equal to 0.65+0.50=1.15. Reducing the Reaction Steam below the 1.15 ratio unquestionably improves the energy efficiency of the styrene process. However, because the feed steam/EB ratio, i.e. composition at any given pressure of the azeotrope, is fixed and cannot be changed, reducing the Reaction Steam can only be accomplished by reducing the heating steam or vaporizing less the 100% of the EB feed as the azeotrope.

Lowering the total amount of reaction steam by reducing heating steam, while vaporizing 100% of the EB as an azeotrope with water, results in heating steam temperatures well beyond the code limits for Incoloy 800H/800 HT metallurgy. To overcome this limitation without resorting to extremely expensive high temperature alloys, the present inventors have discovered that using a three stage reactor system allows the minimum reaction steam/EB ratio to be reduced from 1.15 to 0.90 while simultaneously vaporizing 100% of the EB feed as an azeotrope. Prior to this invention, reducing the reaction steam/EB ratio while practicing azeotrope heat recovery could not be effectively implemented without resorting to the use of tremendously expensive alloys that have not been proven in styrene service.

Conventional two step dehydrogenation processes practiced widely in today's styrene industry require a minimum of about 0.65 to 0.70 kg of heating steam per kilogram (kg) of ethylbenzene feed. The 0.65 to 0.70 kg of heating steam per kilogram (kg) of ethylbenzene feed minimum is required for two purposes: 1) reheating the feed between the primary and secondary reactors due to the highly endothermic nature of the ethylbenzene dehydrogenation reaction; and 2) bringing the primary reactor feed mixture to the required reactor inlet temperature.

This minimum amount of heating steam to EB ratio is set to keep the heating steam temperature below 899° C., which is the maximum allowable temperature for Alloy 800H, which is the industry standard material used for fabrication of high temperature process equipment and transfer lines used in styrene production. When recovering low level heat by vaporizing a minimum boiling azeotrope of water and ethylbenzene, the ratio of water (Feed Steam) to EB is 0.50 wt/wt. Thus, for a two stage reaction system (i.e., conventional two dehydrogenation reactors and one reheater system for the dehydrogenation of EB to styrene monomer) that vaporizes 100% of the EB feed as an azeotrope with water, the minimum total reaction steam is the sum of the minimum heating steam and the feed steam contained in the azeotropic feed which is equal to 0.65+0.50=1.15.

As previously noted, to improve energy efficiency, reducing the heating steam/EB ratio to less than 0.65 kg/kg requires the use of very expensive alloys, which are unproven in the styrene service. Consequently, to be able to couple azeotropic heat recovery, vaporize 100% of the EB feed as an azeotrope, and reduce the total reaction steam (i.e. Steam-to-oil Ratio), as more fully presented herein below, the instantly disclosed flow schemes that provide lower heating steam temperatures are required.

In an embodiment of the invention, a three dehydrogenation reactors two reheater system for the dehydrogenation of EB to styrene monomer is presented. In this embodiment, the "duty" of each of the two reheaters (i.e., reheat exchanger) in the three-reactor system is less than the duty of a reheater in the conventional two-reactor system, even though the total reheat duty is larger. As a result, the heating steam temperature that is supplied to either of the two reheaters in a three-reactor system is substantially lower than the temperature of heating steam necessarily required for the reheater in a traditional two-reactor system. This fact can be derived mathematically as described below.

The reheater duty is equal to the product of the mass flow of the fluid, its heat capacity and the temperature change across the reheater. Furthermore, since the duty is same for the cold (i.e., effluent) and the hot fluid (i.e., steam), it follows that:

$$m_R \cdot c_{P,R} \cdot (T_{o,R} - T_{i,R}) = m_S \cdot c_{P,S} \cdot (T_{i,S} - T_{o,S}) \qquad (1)$$

where m is mass flow, $c_P$, is heat capacity, and T is the temperature. The subscripts R and S refer to the reactants being heated and heating steam, respectively, while i, and o refer to the fluid entering and leaving the reheater.

By rearranging Equation 1, the steam reheater inlet temperature can be determined as follows:

$$T_{i,S} = T_{o,S} + \frac{m_R \cdot c_{P,R}}{m_S \cdot c_{P,S}} (T_{o,R} - T_{i,R}) \qquad (2)$$

Using this relationship, the difference between the temperature of heating steam required for a reheater in a two-reactor system (subscript 2 in Formula (3)) and that required for a reheater in a three-reactor system (subscript 3 in Formula (3)) is:

$$T_{i,S,2} - T_{i,S,3} = T_{o,S,2} - T_{o,S,3} + \frac{m_R \cdot c_{P,R}}{m_S \cdot c_{P,S}} (T_{o,R,2} - T_{i,R,2} - T_{o,R,3} + T_{i,R,3}) \qquad (3)$$

Since the temperature of reactants leaving the reheater (i.e., inlet temperature of the downstream reactor) is same for both two and three-reactor systems, the above formula can be simplified as follows:

$$T_{i,S,2} - T_{i,S,3} = T_{o,S,2} - T_{o,S,3} + \frac{m_R \cdot c_{P,R}}{m_S \cdot c_{P,S}} (T_{i,R,3} - T_{i,R,2}) \qquad (4)$$

Furthermore, if we assume that the cold end temperature approach (the difference between the temperature of steam leaving the reheater and the temperature of the reactants entering the reheater) is the same for both two and three-reactor systems (which is always true for an infinitely large reheater), Equation (4) becomes:

$$T_{i,S,2} - T_{i,S,3} = T_{i,R,2} - T_{i,R,3} - \frac{m_R \cdot c_{P,R}}{m_S \cdot c_{P,S}} (T_{i,R,2} - T_{i,R,3}) \qquad (5)$$

which can be simplified as follows:

$$T_{i,S,2} - T_{i,S,3} = (T_{i,R,2} - T_{i,R,3}) \cdot \left(1 - \frac{m_R \cdot c_{P,R}}{m_S \cdot c_{P,S}}\right) \qquad (6)$$

Finally, since $c_{P,R} \approx c_{P,S}$, $T_{i,R,3} > T_{i,R,2}$, and $m_R$ is a factor of 2 or more larger than $m_S$, it follows that $T_{i,S,2} > T_{i,S,3}$.

Figure 2:
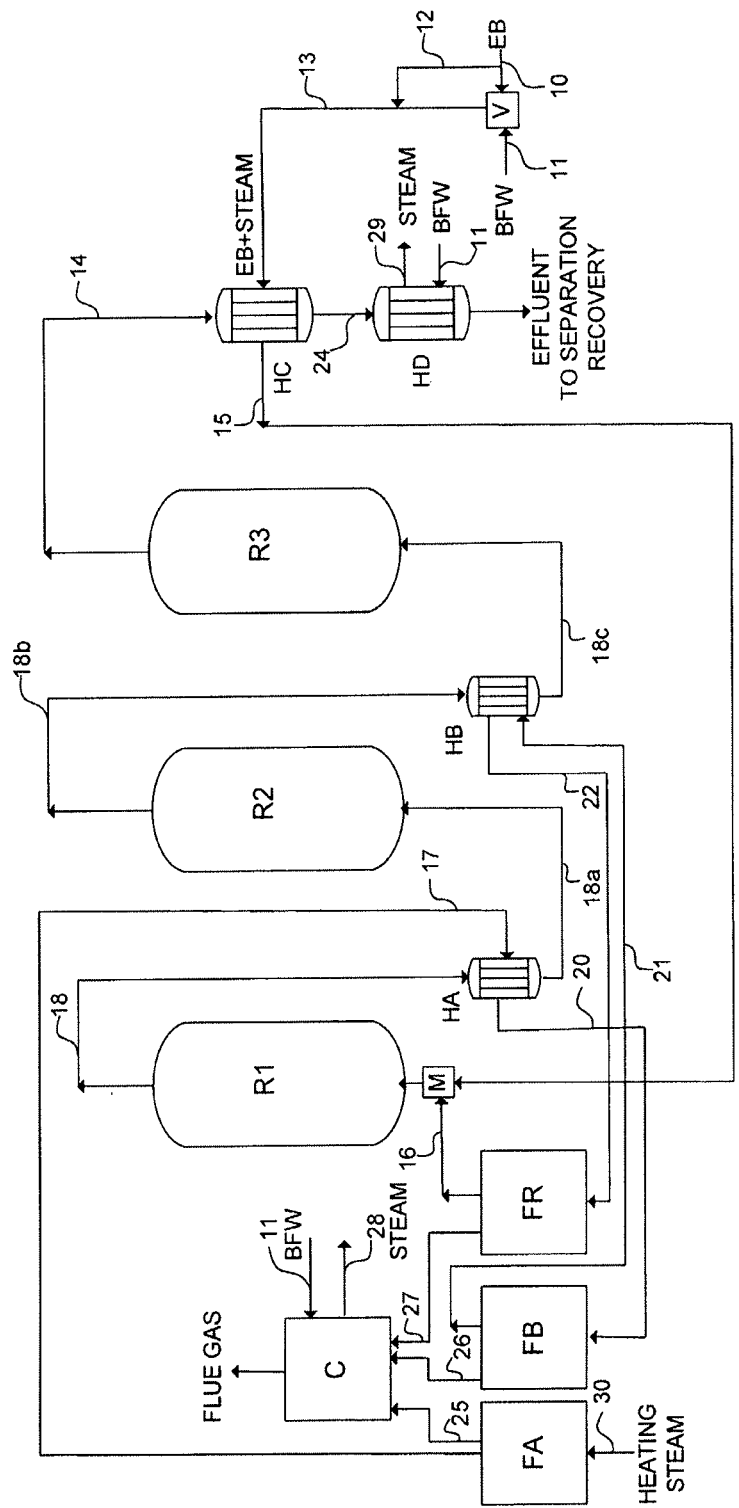
FIG. 2 is a schematic flowsheet illustrating an embodiment of the present invention having a three-reactor system for producing styrene via dehydrogenation of ethylbenzene.
Figure 3:
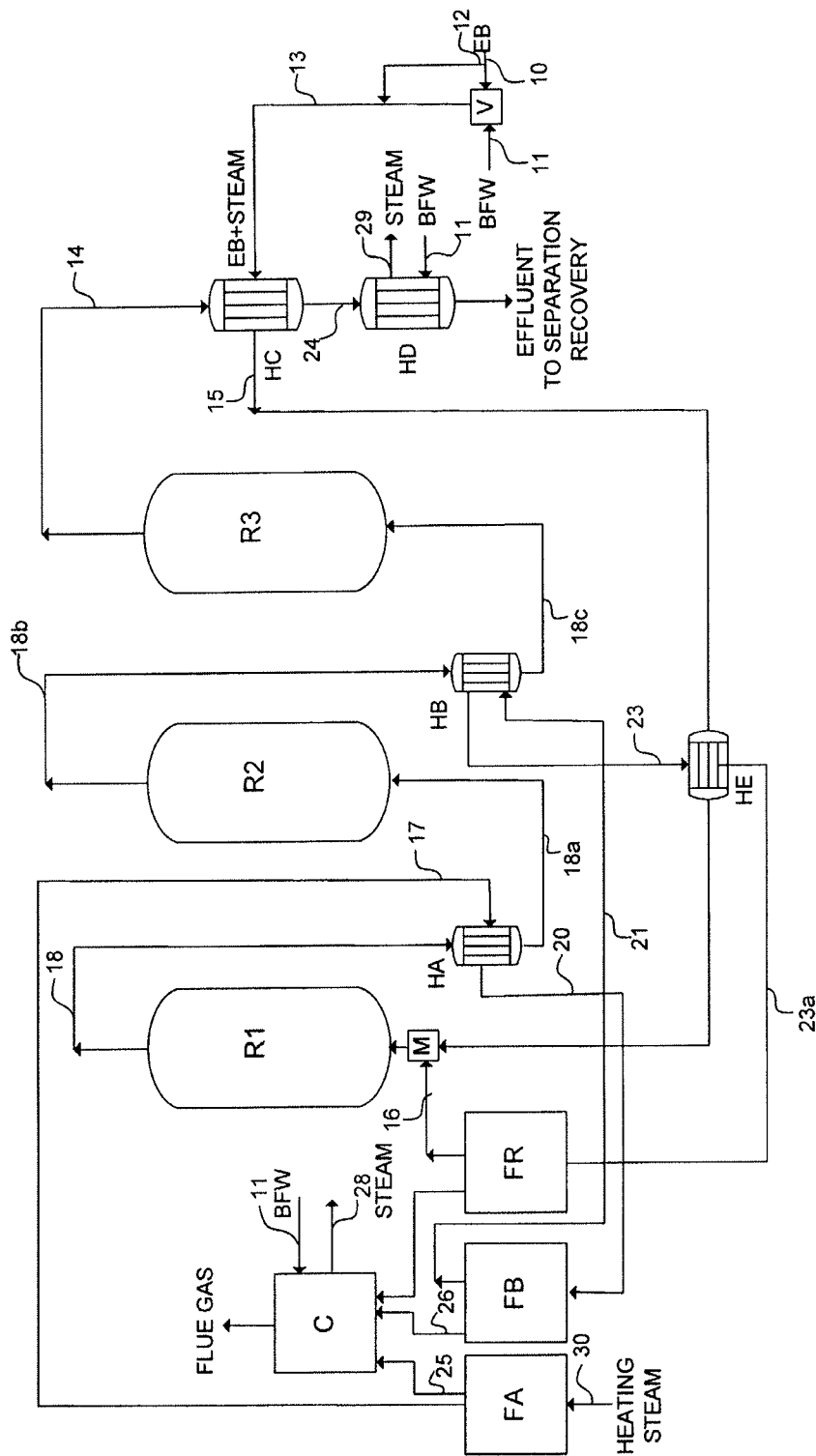
FIG. 3 is an a schematic flowsheet illustrating an embodiment of the present invention having a three-reactor system with a reactor feed preheater for producing styrene via dehydrogenation of ethylbenzene.

Referring to the accompanying FIGS. 1, 2, and 3, the dehydrogenation reaction takes place in a series of reactors with an intermediate reheating step(s). Ethylbenzene (EB) 10 and water (BFW) 11 are vaporized as a low boiling point azeotrope in the azeotropic vaporizer V using a convenient heat source (not shown), such as the overhead vapor from the crude styrene column (also referred to as EB/SM splitter and as EB recycle column). Typical azeotropic vapor mixture of EB and water consists of 2 parts of EB to 1 part of water vapor by weight. This water vapor is referred to herein as "feed steam." The ratio of feed steam to EB is controlled by way of bypassing a portion of the EB 12 around the azeotropic vaporizer V, as noted in FIGS. 1-3. Since this feed steam is essentially "free," as being generated using heat that would otherwise be rejected to cooling water or air, it is advantageous to minimize the amount of EB 12 bypassing the azeotropic vaporizer V.

The reactor feed 13, i.e., the azeotropic mixture plus EB bypass, is superheated against the effluent 14 leaving the last dehydrogenation reactor R2 in FIG. 1, and R3 in FIGS. 2 and 3, respectively, in the feed effluent exchanger HC. The reactor feed stream 15 leaving effluent exchanger HC is mixed in a mixing apparatus (e.g., a mixing vessel) M with additional steam 16 that is heated in reactor superheater FR to a temperature sufficiently high to bring the resulting mixture to proper reactor inlet temperature, typically 600-650° C. This steam is referred to herein as "heating steam."

The heating steam 30 is first heated in the primary superheater FA. From there the heating steam 17 is directed to the primary reheater HA, where it gives up part of its heat to reheat the reactor R1 effluent 18, 18a, prior to it entering the second reactor R2.

In the prior art process of FIG. 1, heating steam 19 leaving the reheater HA flows directly to the reactor steam superheater FR, where it is heated again and becomes steam 16 prior to being mixed with EB in mixing vessel M. In the improved process, as displayed in FIGS. 2-3, a third reactor, i.e., tertiary dehydrogenation reactor R3, is added. The addition of tertiary dehydrogenation reactor R3 requires a second reheat step of dehydrogenation reactor R2 effluent 18b, 18c, which is carried out in the secondary reheater HB prior to entering tertiary dehydrogenation reactor R3 (see FIGS. 2 and 3). In FIGS. 2 and 3 the heating steam 21 entering secondary reheater HB is the steam 20 leaving primary reheater HA after it has been heated in the secondary steam superheater FB. In FIG. 2 the steam 22 leaving secondary reheater HB is heated in reactor steam superheater FR and becomes steam 16 before being mixed with the reactor feed 15 in mixing vessel M (see FIG. 2). This step is analogous to the prior art flowsheet, except that the steam feeding reactor steam superheater FR comes from secondary reheater HB instead of primary reheater HA. In FIG. 3, the steam 23 leaving secondary reheater HB is directed to an optional feed stream 15 preheater exchanger HE where it gives up part of its heat to heat reactor feed stream 15 prior to entering mixing apparatus M. The steam 23a leaving optional preheater exchanger HE is heated in reactor steam superheater FR, before being mixed with the reactor stream 15 in mixing vessel M.

The heat remaining in the reactor effluent 24 leaving the feed effluent exchanger HC is used to generate steam 29 in the steam generator HD. Likewise, the hot flue gas 25, 26, and 27 from the steam superheaters FA, FB, and FR, respectively, is collected in a common convection section C, where its heat is used for steam 28 generation.

EXAMPLES

The key parameters for the following examples are summarized in Table 1 herein below.

Example 1 illustrates the conditions in the prior art two-reactor process system. See FIG. 1.

The entire EB feed is co-vaporized with water in the azeotropic vaporizer V. The mixture, which contains 0.5 kg of feed steam per kg of EB, is heated to 553° C. on the shell side of feed effluent exchanger HC against the effluent from R2, which enters feed effluent exchanger HC at a temperature of 593° C.

Downstream of feed effluent exchanger HC, the feed mixture is combined in mixing vessel M with heating steam that is heated in reactor steam superheater FR to a temperature of 899° C. This is the maximum temperature at which a vessel constructed out of Alloy 800H (a standard nickel alloy used in the styrene process) can operate, as specified by ASME codes. The amount of heating steam necessary to keep reactor steam superheater FR steam outlet temperature at no higher than 899° C., while achieving a mix temperature of 650° C. (when added to a 553° C. mixture EB and feed steam) is equivalent to 0.65 kg per kg of ethylbenzene feed.

A portion of the ethylbenzene is converted to styrene and other byproducts in R1, and the resulting effluent leaves R1 at a temperature of 565° C. It is subsequently reheated to a temperature of 650° C. in the primary reheater HA. Heating steam enters the primary reheater HA at a temperature of 899° C. (maximum for Alloy 800H) and leaves at a temperature of 597° C. Even with an infinitely large heat exchanger (i.e., reheater), the temperature of steam that is required to heat the reactor effluent in this example to 650° C. is 869° C., which is the reactor effluent inlet temperature plus heating steam temperature drop across the reheater.

In view of the fact that styrene dehydrogenation catalyst can operate at an overall steam-to-oil ratio of less than 1.15, and as low as 0.85, it is advantageous to reduce the amount of heating steam required by the process and thereby reduce the overall energy requirements. However, as illustrated by this example, a substantial reduction of heating steam below 0.65 kg per kg EB is not possible using the prior art two-reactor process because it would require reactor steam superheater FR steam outlet temperature to be greater than 899° C.

Example 2, illustrates that the improved process and system of the present invention allows for a reduction in heating steam. Example 2 is demonstrated by the schematic flow sheet presented in FIG. 2.

The total flow of EB, i.e., 106728 kg/hr is the same as in Example 1, as are the 650° C. reactor inlet temperatures. However, the amount of heating steam is reduced by approximately 23% (i.e., 0.650 to 0.500) compared with Example 1, thus the ratio heating steam to EB is 0.50 kg per kg, see Table 1.

For this example, the primary reheater HA is the same size as used in Example 1, and the secondary reheater HB is $\frac{1}{3}^{rd}$ the size of primary reheater HA. Despite the fact that approximately 23% less heating steam is available for reheating the primary reactor effluent, the required steam inlet temperature from steam super heater FA is actually 6° C. lower than Example 1, see FA Outlet Temperature of Examples 1 and 2 in Table 1, 899° C. and 893° C., respectively.

Since the secondary reheater HB duty is smaller than the duty of primary reheater HA, a much smaller exchanger is sufficient to heat the tertiary dehydrogenation reactor R3 to a temperature of 650° C. In this example, the surface area in secondary reheater HB is $\frac{1}{3}^{rd}$ that of primary reheater HA and despite being so much smaller, the required steam inlet temperature is only 876° C.

With the amount of heating steam being reduced by approximately 23%, the temperature of the EB and feed steam leaving effluent exchanger HC has to be increased from 553° C. to 576° C. in order to keep the outlet temperature of steam superheater FR within the limits of Alloy 800H. This can be accomplished by several means, such as by passing the EB/feed steam mixture through a coil (not shown in Figures) in the common convection section C, to heat the EB and feed steam prior to entering the reactor, or by adding a reactor feed preheater exchanger HE, see FIG. 3, in which the feed mixture is heated by the heating steam leaving the secondary reheater HB.

Yet another way of increasing the temperature of the EB/feed steam mixture prior to mixing with the heating steam in the mixing vessel M is to increase the size of the feed effluent exchanger HC, which is the method employed in this example. Since the temperature of the reactor effluent entering this exchanger is substantially higher than in Example 1, the size of effluent exchanger HC has to be increased by approximately 12%. As will be illustrated in the next example, this increase is much less than what is required for a two-reactor system.

The improvements made possible by the process and system of the current invention reduce the energy requirements by 15% compared to prior art, as indicated by the data in Table 1, see e.g., Net Heat Input.

Example 3 utilizes the process configuration as presented in Example 1, i.e., FIG. 1, which is representative of the prior art process.

The total flow of EB, i.e., 106728 kg/hr and the reactor inlet temperatures are also the same as in Example 1. Despite increasing the size of the primary reheater HA by 28%, the required steam outlet FA temperature goes up to 955° C., far above what is permitted for Alloy 800H. It therefore is clear that, in order for a two-reactor system to match the same energy efficiency as a three-reactor system of this invention, the reheater must be constructed using very expensive alloys that are unproven in the styrene service.

As presented in Example 2, to keep the outlet temperature of the reactor steam superheater FR within what is allowed by industry code for Alloy 800H, the size of the feed effluent exchanger HC has to be increased. In this case, however, because the R2 reactor effluent temperature is substantially colder than in the process of this invention, i.e., the R3 reactor effluent of Example 2, which is representative of the present invention, is 27° C. colder, see Table 1. Thus, the size of the Example 3 feed effluent exchanger HC must be increased by a factor of 2 compared with Example 1. Specifically, the 8200 feed effluent exchanger HC area (m$^2$) is substantially doubled to 16300 in Example 3, whereas the feed effluent exchanger HC area (m$^2$) of inventive Example 2 is merely increased by approximately 12% to 9200.

In Example 4, which also illustrates the limitations of the prior-art method and system, the amount of heating steam is increased by 20% while maintaining the total amount of reaction steam the same as in Examples 2 and 3, i.e., the ratio Reaction Steam/EB 1.0000, see Table 1. Although this change makes it possible to use Alloy 800H for the reheater and reduces the size of feed effluent exchanger HC area (m$^2$) to 8800, as compared with Example 3, this comes at the price of increased energy consumption, see Net Heat Input for Examples 3 and 4 in Table 1. This is because 20% of the EB feed has to be bypassed around the azeotropic vaporizer V (Example 4% EB Vaporized in V is 80%, see Table 1), thus reducing the amount of steam generated in steam generator HD. Compared with Example 2, which illustrates the advantages of the three-reactor system, the net energy consumption of this example increases by 15%.

Example 5 further illustrates the capability of the improved method and process of the current invention in terms of energy reduction, the ratio of heating steam to EB is decreased to 0.4 while still vaporizing 100% of the EB feed as the azeotrope (i.e., vaporizing all of the EB in V). To accomplish this, the size of both reheaters is increased compared with Example 2. Specifically, primary reheater HA surface area (m$^2$) is increased by approximately 11% from 1800 in Example 2 to 2000 in Example 5. Similarly, secondary reheater HB is increased by a factor of 2, i.e., secondary reheater HB surface area (m²) is double from 600 to 1200, and the size of the feed effluent exchanger HC surface area (m²) is increased by approximately 61% to 14800.

The net result is a further approximate 12% reduction in energy consumption compared with Example 2 (see Table 1: Net Heat Input is reduced from 527 to 465, respectively) while staying below the code limit temperatures of Alloy 800H. Overall this translates to a 25% reduction in energy consumption compared with what is possible using prior art.

TABLE 1

|  | Example 1 Prior Art Method | Example 2 Claimed Method | Example 3 Prior Art Method | Example 4 Prior Art Method | Example 5 Claimed Method |
|---|---|---|---|---|---|
| Number of Reactors | 2 | 3 | 2 | 2 | 3 |
| HA Area (m²) | 1800 | 1800 | 2300 | 2300 | 2000 |
| HB Area (m²) | NA | 600 | NA | NA | 1200 |
| HC Area (m²) | 8200 | 9200 | 16300 | 8800 | 14800 |
| HD Area (m²) | 3100 | 2700 | 2400 | 2700 | 2200 |
| HE Area (m²) | NA | NA | NA | NA | 0 |
| Total EB Flow, kg/hr | 106728 | 106728 | 106728 | 106728 | 106728 |
| HA Area (relative) | 1.00 | 1.00 | 1.28 | 1.28 | 1.11 |
| HB Area (relative) | NA | 0.33 | NA | NA | 0.67 |
| HC Area (relative) | NA | NA | NA | NA | 0.00 |
| % EB Vaporized in V | 100% | 100% | 100% | 80% | 100% |
| Heating Steam/EB (kg/kg) | 0.650 | 0.500 | 0.500 | 0.600 | 0.400 |
| Azeotropic Feed Steam/EB (kg/kg) | 0.500 | 0.500 | 0.500 | 0.400 | 0.500 |
| Reaction Steam/EB (kg/kg) | 1.150 | 1.000 | 1.000 | 1.000 | 0.900 |
| Net Steam Required/EB (kg/kg) (i.e. the amount of Heating Steam required) | 0.650 | 0.500 | 0.500 | 0.600 | 0.400 |
| Percent EB Conversion | 64% | 64% | 64% | 64% | 64% |
| R1 Inlet Temperature (° C.) | 650 | 650 | 650 | 650 | 650 |
| R1 Outlet Temperature (° C.) | 565 | 582 | 560 | 560 | 577 |
| R2 Inlet Temperature (° C.) | 650 | 650 | 650 | 650 | 638 |
| R2 Outlet Temperature (° C.) | 593 | 602 | 589 | 589 | 593 |
| R3 Inlet Temperature (° C.) | NA | 650 | NA | NA | 650 |
| R3 Outlet Temperature (° C.) | NA | 616 | NA | NA | 611 |
| FA Outlet Temperature (° C.) | 899 | 893 | 955 | 899 | 899 |
| FB Inlet Temperature (° C.) | NA | 668 | NA | NA | 603 |
| FB Outlet Temperature (° C.) | NA | 876 | NA | NA | 899 |
| FR Inlet Temperature (° C.) | 597 | 595 | 567 | 572 | 580 |
| FR Outlet Temperature (° C.) | 899 | 899 | 899 | 899 | 899 |
| HC Feed Outlet Temp (° C.) | 553 | 576 | 576 | 555 | 591 |
| HA Cold End Approach (° C.) | 32 | 14 | 7 | 12 | 4 |
| HB Cold End Approach (° C.) | NA | 66 | NA | NA | 9 |
| HC Cold End Approach (° C.) | NA | NA | NA | NA | 308 |
| FA Absorbed Q (kcal/kg EB) | 252.0 | 192.2 | 210.3 | 232.7 | 155.2 |
| FR Absorbed Q (kcal/kg EB) | NA | 76.7 | NA | NA | 69.8 |
| FC Absorbed Q (kcal/kg EB) | 107.6 | 64.0 | 90.6 | 107.2 | 65.1 |
| FA Fired Q (kcal/kg EB) | 280.0 | 213.5 | 233.6 | 258.5 | 172.4 |
| FB Fired Q (kcal/kg EB) | NA | 170.5 | NA | NA | 155.0 |
| FR Fired Q (kcal/kg EB) | 239 | 142 | 201 | 238 | 145 |
| Total Fired Duty (kcal/kg EB) | 519 | 526 | 435 | 497 | 472 |
| Heating Steam to FA (kcal/kg EB) | 357 | 275 | 275 | 330 | 220 |
| Steam Credit—Cony Section C (kcal/kg EB) | 108 | 141 | 91 | 107 | 135 |
| Steam Credit—Generator HD (kcal/kg EB) | 159 | 134 | 101 | 124 | 91 |
| Net Heat Input (as Fuel) (kcal/kg EB) | 619 | 527 | 527 | 607 | 465 |

Although the present invention has been described in considerable detail with regard to certain versions thereof, other versions are possible, and alterations, permutations, and equivalents of the version shown will become apparent to those skilled in the art upon a reading of the specification and study of the drawings. Also, the various features of the versions herein can be combined in various ways to provide additional versions of the present invention. Furthermore, certain terminology has been used for the purposes of descriptive clarity, and not to limit the present invention. Therefore, any appended claims should not be limited to the description of the preferred versions contained herein and should include all such alterations, permutations, and equivalents as fall within the true spirit and scope of the present invention.

What is claimed is:

1. A method for reducing the amount of steam used in a dehydrogenation section of an alkenyl aromatic hydrocarbon production facility, said dehydrogenation section for dehydrogenating ethylbenzene to styrene monomer, said method comprising:
   i) heating a feed stream comprising ethylbenzene and water as an azeotrope to provide an ethylbenzene/feed steam stream containing vaporized ethylbenzene and feed steam having a feed steam to ethylbenzene ratio of about 0.4 wt/wt to about 0.6 wt/wt;
   ii) mixing the ethylbenzene/feed steam stream with heating steam from a steam superheater;
   iii) supplying the ethylbenzene/feed steam stream and heating steam to a first reactor in the dehydrogenation section;
   iv) dehydrogenating the ethylbenzene in the first reactor, a second reactor, and at least a third reactor of the dehydrogenation section to produce styrene monomer; and v) reheating an effluent from the first reactor in at least a first reheat exchanger and an effluent from the second reactor in at least a second reheat exchanger,
wherein each reheat exchanger is provided with heating steam from at least one steam superheater, said heating steam having a temperature of less than about 899° C. and said method utilizing a total heating steam to ethylbenzene ratio of less than about 0.65 wt/wt.

2. The method of claim 1, wherein the feed stream comprising ethylbenzene and water are vaporized as an azeotrope in an azeotropic vaporizer.

3. The method of claim 1, wherein the mixing of the ethylbenzene/feed steam stream and heating steam takes place in a mixing apparatus prior to entering the first reactor.

4. The method of claim 1, wherein the ethylbenzene/feed steam stream is heated in a preheater exchanger with heating steam from the second reheat exchanger prior to entering the first reactor.

5. The method of claim 1, wherein the ethylbenzene/feed steam stream is heated in an effluent exchanger with an effluent from the third reactor prior to entering the first reactor.

6. The method of claim 1, wherein the first reheat exchanger has a surface area that is the same or larger than the surface area of the second reheat exchanger.

7. The method of claim 1, wherein the heating steam to ethylbenzene ratio is from about 0.45 wt/wt to about 0.55 wt/wt.

8. The method of claim 1, wherein the heating steam to ethylbenzene ratio is about 0.50 wt/wt.

9. The method of claim 1, wherein the combined ratios of feed steam to ethylbenzene and heating steam to ethylbenzene is less than about 1.00.

10. The method of claim 1, wherein the method utilizes a system and the system sequentially comprises: a means for heating a feed stream comprising ethylbenzene and water as an azeotrope to provide an ethylbenzene/feed steam stream containing vaporized ethylbenzene and feed steam having a feed steam to ethylbenzene ratio of about 0.4 wt/wt to about 0.6 wt/wt; a mixing apparatus for mixing the ethylbenzene/feed steam stream with superheated heating steam, said heating steam is utilized as a heating medium; a means for supplying the ethylbenzene/feed steam stream and heating steam to a first dehydrogenation reactor to provide effluent to a first reheat exchanger for reheating said effluent prior to entering a second dehydrogenation reactor and providing a second reactor effluent that is reheated in a second reheat exchanger prior to entering a third dehydrogenation reactor to provide styrene monomer, said first and second reheat exchangers utilize superheated heating steam as a heating medium,
wherein the heating steam has a temperature of less than about 899° C. and said system utilizes a total heating steam to ethylbenzene ratio of less than about 0.65 wt/wt.

11. The method of claim 10, wherein the feed stream comprising ethylbenzene and water are vaporized as an azeotrope in an azeotropic vaporizer.

12. The method of claim 10, wherein the ethylbenzene/feed steam stream is heated in a preheater exchanger with heating steam from the second reheat exchanger prior to entering the first reactor.

13. The method of claim 10, wherein the ethylbenzene/feed steam stream is heated in an effluent exchanger with an effluent from the third reactor prior to entering the first reactor.

14. The method of claim 10, wherein the first reheat exchanger has an surface area that is the same or larger than the surface area of the second reheat exchanger.

15. The method of claim 10, wherein the heating steam to ethylbenzene ratio is from about 0.45 wt/wt to about 0.55 wt/wt.

16. The method of claim 10, wherein the heating steam to ethylbenzene ratio is about 0.50 wt/wt.

17. The method of claim 10, wherein the combined ratios of feed steam to ethylbenzene and heating steam to ethylbenzene is less than about 1.00 wt/wt.

18. The method of claim 10, wherein said means for heating a feed stream comprising ethylbenzene and water and said means for supplying the ethylbenzene/feed steam flow stream and heating steam to the dehydrogenation reactors are constructed of Incoloy 800 H/800 HT metallurgy or 304 H stainless steel.

19. A method for reducing the amount of steam used in a dehydrogenation section of an alkenyl aromatic hydrocarbon production facility, said dehydrogenation section used for dehydrogenating ethylbenzene to styrene monomer, said method comprising:
   i) heating a feed stream comprising ethylbenzene and water as an azeotrope to provide an ethylbenzene/feed steam stream containing vaporized ethylbenzene and feed steam having a feed steam to ethylbenzene ratio of about 0.4 wt/wt to about 0.6 wt/wt; and
   ii) dehydrogenating the ethylbenzene in the dehydrogenation section comprising at least a first, second, and a third reactor, at least two reheat exchangers, and a mixing apparatus upstream of the first reactor, said reheat exchangers utilizing superheated heating steam as a heating medium, and said mixing apparatus being used for mixing of heating steam with the ethylbenzene/feed steam stream;
   wherein the temperature of the heating steam in the dehydrogenation section is less than about 899° C., and heating steam to ethylbenzene ratio of less than about 0.65 wt/wt.

20. The method of claim 19, wherein the heating steam to ethylbenzene ratio is about 0.50 wt/wt.

* * * * *